United States Patent
Takatori et al.

(10) Patent No.: US 11,304,625 B2
(45) Date of Patent: Apr. 19, 2022

(54) GAS SENSOR KIT AND DEVICE WEARABLE ON FACE

(71) Applicant: Nihon Kohden Corporation, Tokyo (JP)

(72) Inventors: Fumihiko Takatori, Tokyo (JP); Masayuki Inoue, Tokyo (JP); Kenichiro Kabumoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 600 days.

(21) Appl. No.: 16/087,319

(22) PCT Filed: Jun. 2, 2017

(86) PCT No.: PCT/JP2017/020704
§ 371 (c)(1),
(2) Date: Sep. 21, 2018

(87) PCT Pub. No.: WO2017/217262
PCT Pub. Date: Dec. 21, 2017

(65) Prior Publication Data
US 2019/0099111 A1    Apr. 4, 2019

(30) Foreign Application Priority Data

Jun. 14, 2016 (JP) .............................. JP2016-117759

(51) Int. Cl.
*A61M 16/00* (2006.01)
*A61B 5/097* (2006.01)
(Continued)

(52) U.S. Cl.
CPC .............. *A61B 5/097* (2013.01); *A61B 5/082* (2013.01); *A61B 5/6803* (2013.01);
(Continued)

(58) Field of Classification Search
CPC ....... A61B 5/097; A61B 5/082; A61B 5/6803; A61B 5/6819; A61B 2560/0443;
(Continued)

(56) References Cited

U.S. PATENT DOCUMENTS

| 4,573,462 A | 3/1986 | Aktiengesellschaft |
| 7,044,129 B1 * | 5/2006 | Truschel ............... A61M 16/12 128/204.18 |

(Continued)

FOREIGN PATENT DOCUMENTS

| CN | 202951074 U | 5/2013 |
| JP | 2004-321721 A | 11/2004 |

(Continued)

OTHER PUBLICATIONS

International Search Report issued in Patent Application No. PCT/JP2017/020704 dated Aug. 30, 2017.
(Continued)

*Primary Examiner* — Steven O Douglas
(74) *Attorney, Agent, or Firm* — Pearne & Gordon LLP

(57) ABSTRACT

A gas sensor kit includes a gas sensor that measures a gas concentration of an exhalation gas of a subject, a gas introduction part that introduces the exhalation gas of the subject to the gas sensor and a gas supply unit that supplies a therapeutic gas to the subject. In the gas sensor kit, the gas supply unit includes a flow rate adjusting part that adjusts flow rate of the therapeutic gas.

14 Claims, 10 Drawing Sheets

(51) Int. Cl.
*A61M 16/08* (2006.01)
*A61M 16/04* (2006.01)
*A61B 5/08* (2006.01)
*A61M 16/06* (2006.01)
*A61B 5/00* (2006.01)

(52) U.S. Cl.
CPC .... *A61M 16/0488* (2013.01); *A61M 16/0666* (2013.01); *A61M 16/0672* (2014.02); *A61M 16/085* (2014.02); *A61M 16/0858* (2014.02); *A61B 5/6819* (2013.01); *A61B 2560/0443* (2013.01); *A61M 2202/0208* (2013.01); *A61M 2230/43* (2013.01)

(58) Field of Classification Search
CPC ............ A61M 16/0672; A61M 16/085; A61M 16/0858; A61M 16/0488; A61M 16/0666; A61M 2202/0208; A61M 2230/43
See application file for complete search history.

(56) References Cited

U.S. PATENT DOCUMENTS

| | | |
|---|---|---|
| 2002/0029004 A1 | 3/2002 | Starr et al. |
| 2004/0206907 A1 | 10/2004 | Yamamori et al. |
| 2006/0247551 A1 | 11/2006 | Yamamori et al. |
| 2008/0196715 A1 | 8/2008 | Yamamori |
| 2008/0319334 A1 | 12/2008 | Yamamori |
| 2009/0320851 A1 | 12/2009 | Selvarajan et al. |
| 2010/0078024 A1* | 4/2010 | Andrieux ......... A61M 16/1015 128/204.21 |
| 2010/0317987 A1 | 12/2010 | Inoue et al. |
| 2013/0074845 A1 | 3/2013 | Smith et al. |
| 2015/0128954 A1 | 5/2015 | Smith et al. |
| 2016/0015916 A1 | 1/2016 | Goff et al. |
| 2018/0339123 A1 | 11/2018 | Smith et al. |
| 2019/0269872 A1 | 9/2019 | Smith et al. |

FOREIGN PATENT DOCUMENTS

| | | |
|---|---|---|
| JP | 2008-200061 A | 9/2008 |
| JP | 5385599 B2 | 1/2014 |
| JP | 2016-000265 A | 1/2016 |

OTHER PUBLICATIONS

Written Opinion issued in Patent Application No. PCT/JP2017/020704 dated Aug. 30, 2017.

Nihon Kohden Corporation, "CO2 Sensor Kit", URL: http://www.nihonkohden.co.jp/iryo/products/monitor/01_bedside/tg970p.html, Accessed May 31, 2016.

Japanese Office action issued in Japanese Patent Application No. 2016-117759 dated Jun. 2, 2020.

* cited by examiner

[Fig. 1]
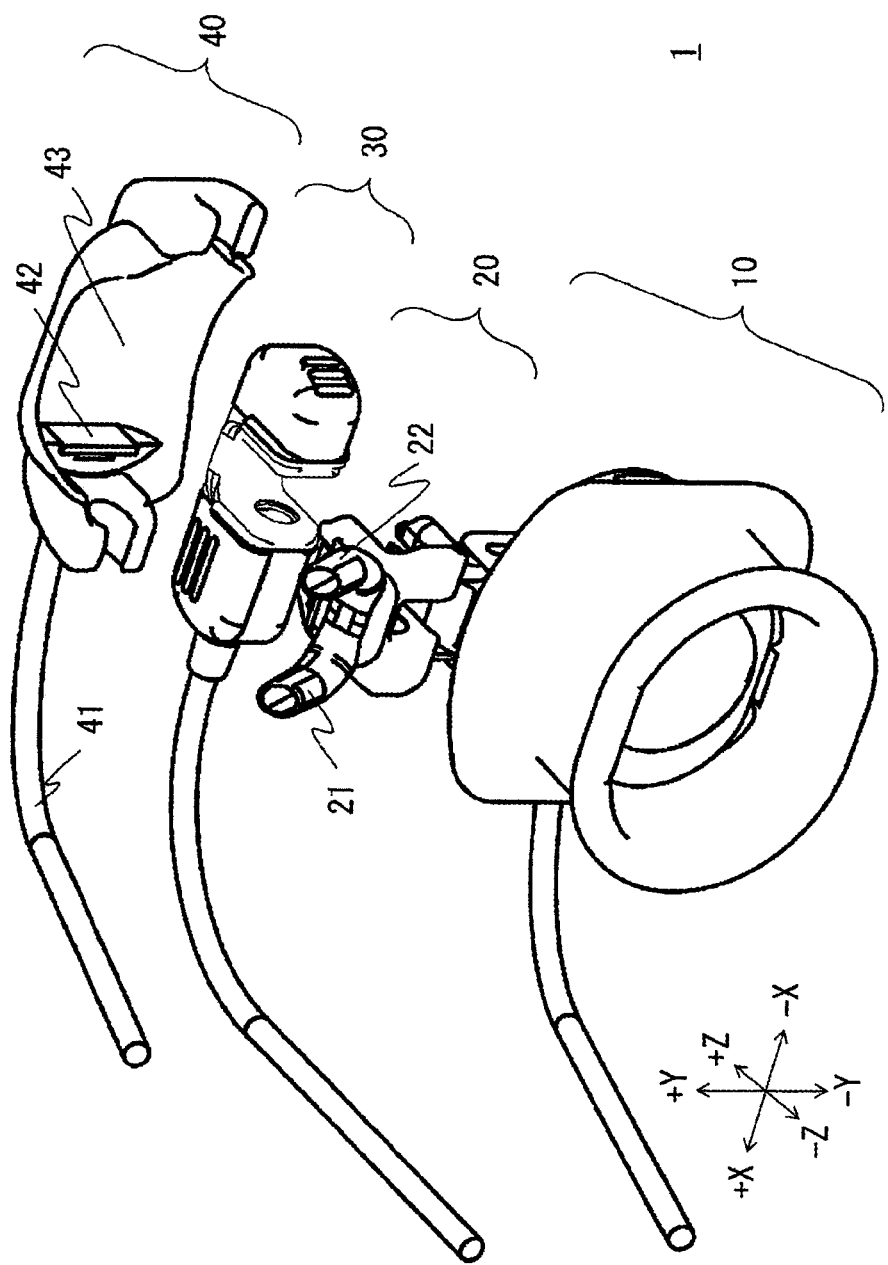

[Fig. 2]
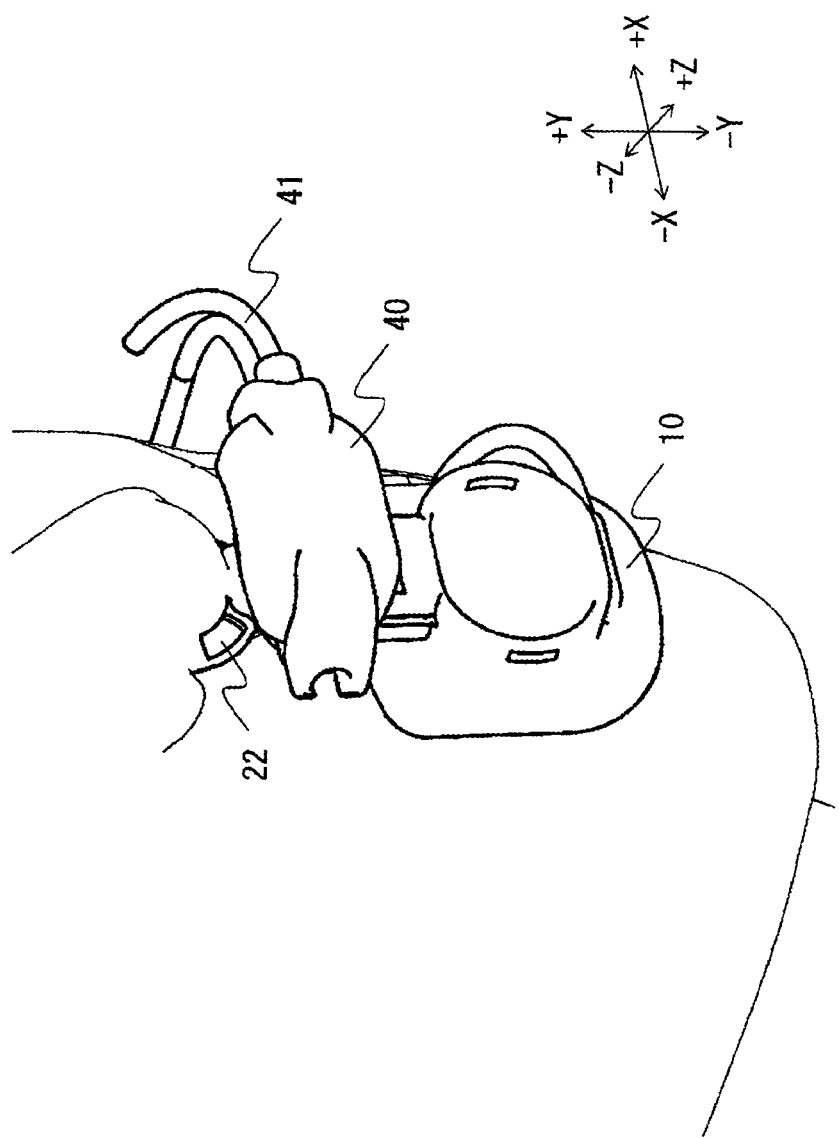

[Fig. 3]
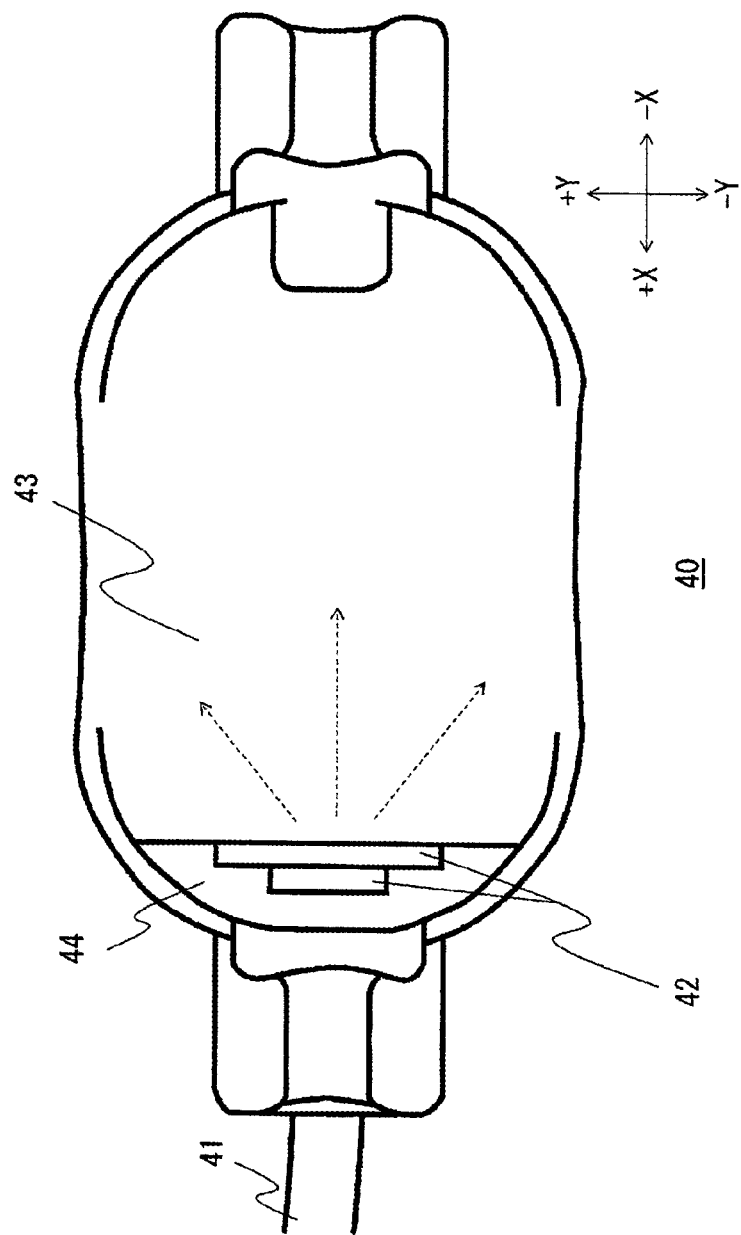

[Fig. 4]
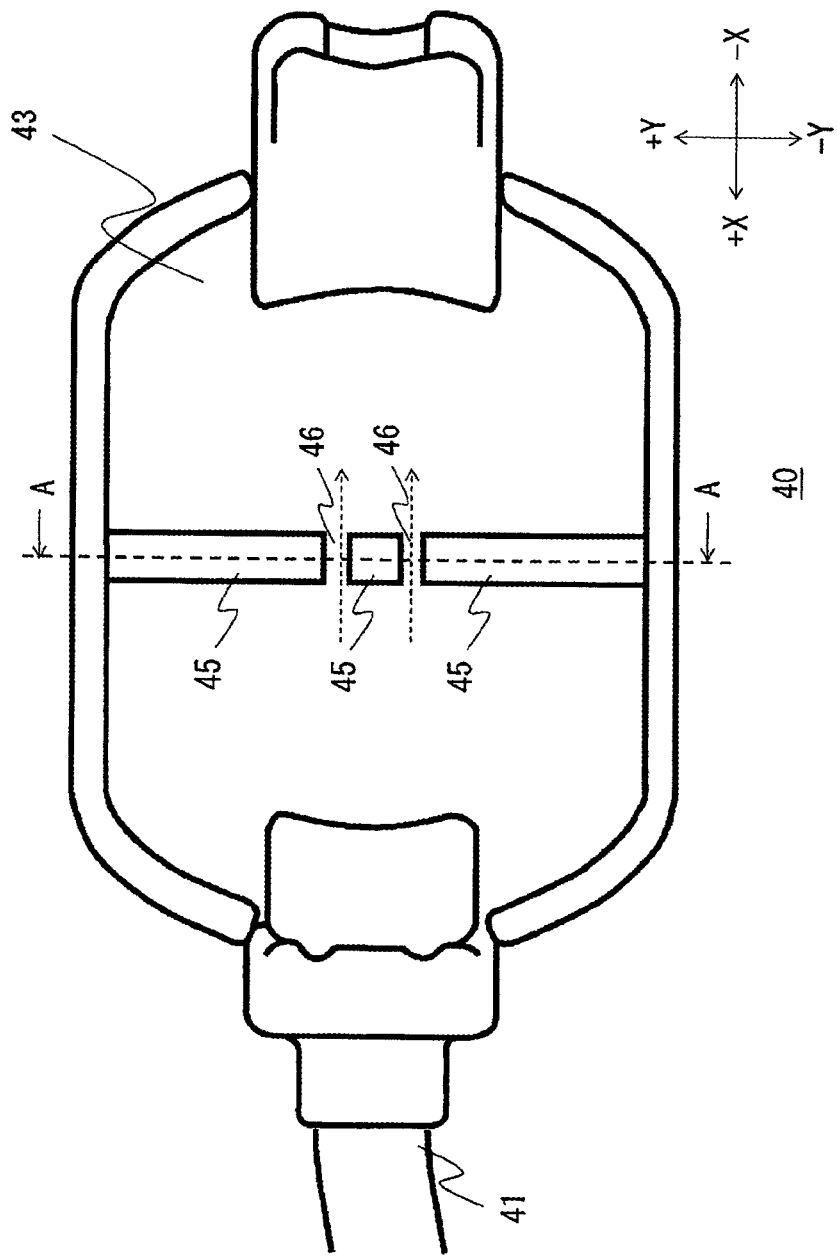

[Fig. 5]
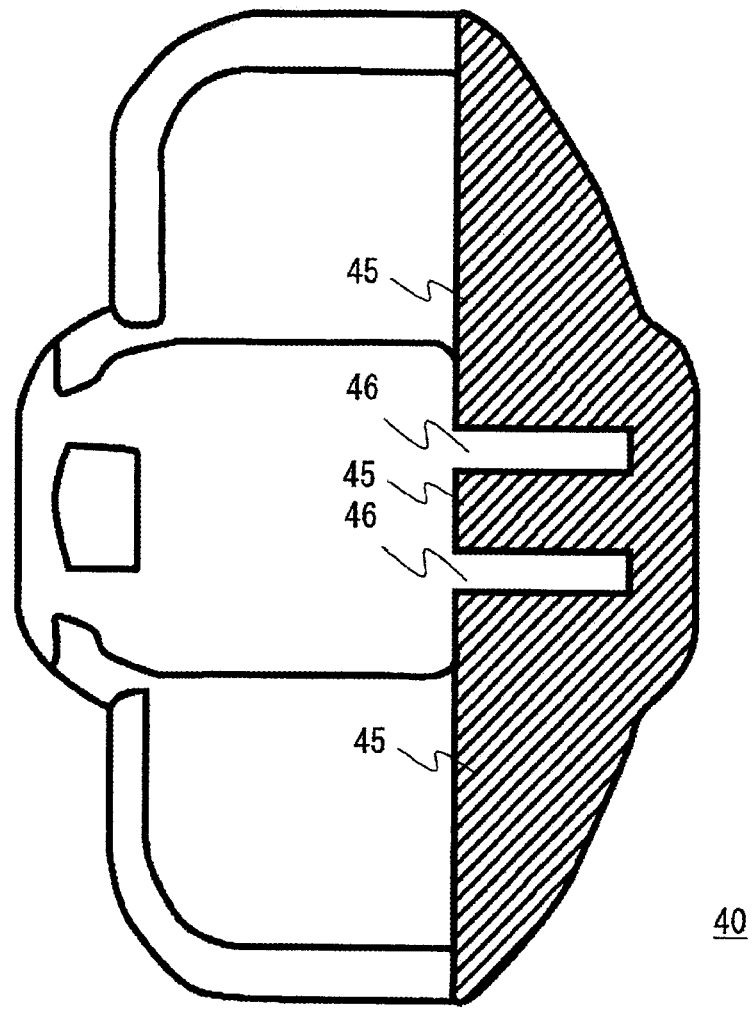
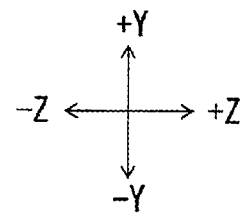

[Fig. 6]
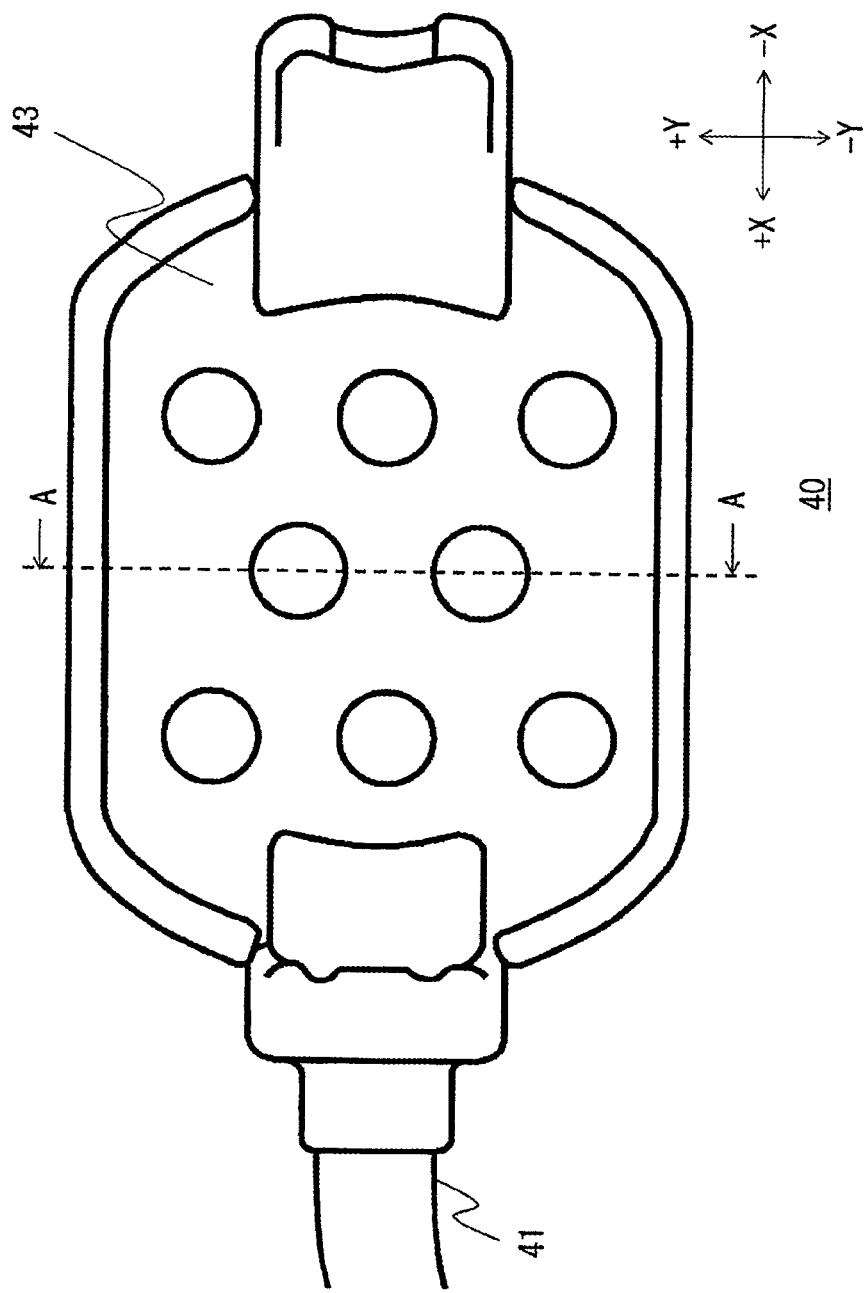

[Fig. 7]
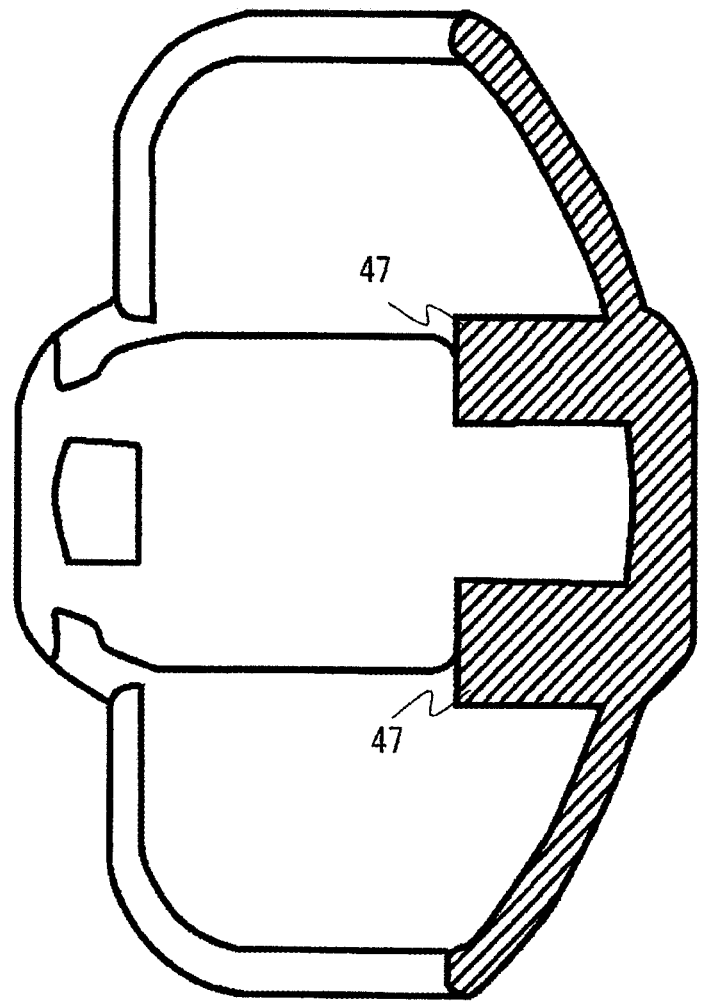
40
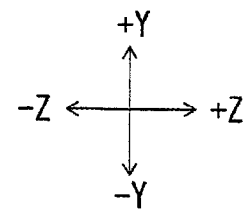

[Fig. 8]
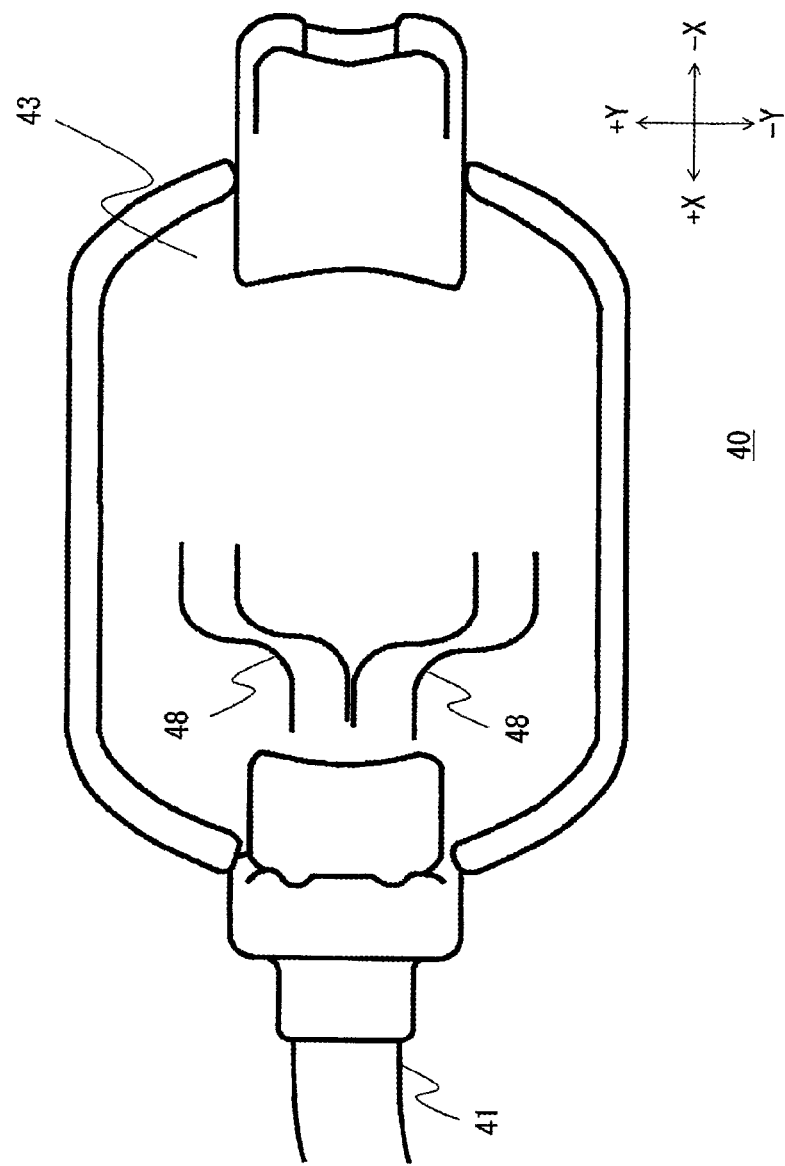

[Fig. 9A]
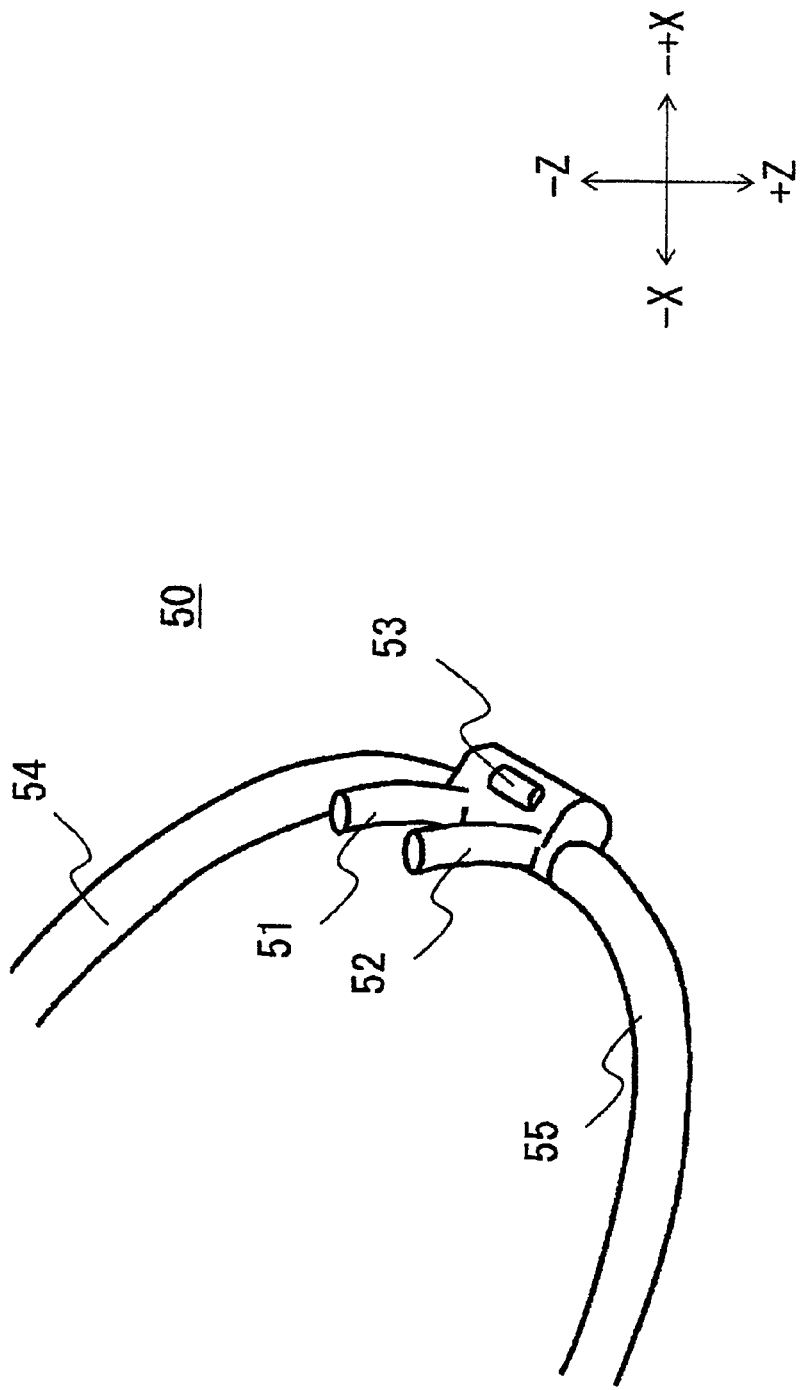

[Fig. 9B]
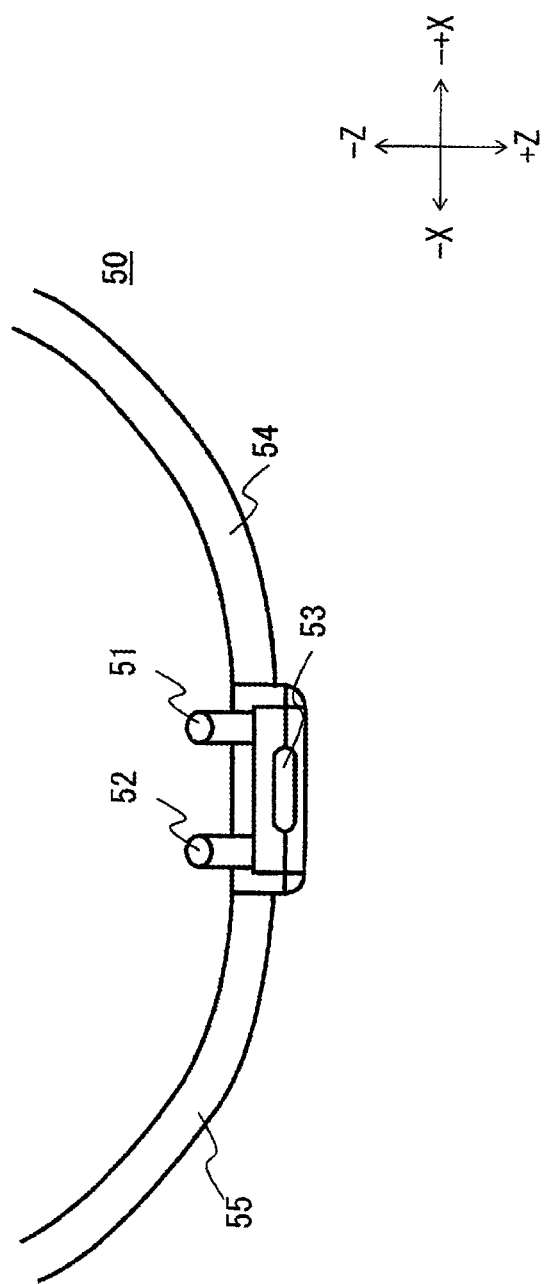

GAS SENSOR KIT AND DEVICE WEARABLE ON FACE

TECHNICAL FIELD

The present invention relates to a gas sensor kit and a device wearable on a face.

BACKGROUND ART

As a symptomatic therapy with respect to a subject in a low-oxygen state, a method administering high concentration oxygen gas with an oxygen mask or an oxygen cannula is used. In the case of performing a treatment with respect to the subject in the low-oxygen state, it is necessary to perform both the administration of the high concentration oxygen gas and the measurement of a respiratory state (exhalation gas concentration) of the subject.

PTL 1 discloses a bite block which accurately measures the respiratory state of the subject by avoiding an effect of secretion such as saliva. The bite block includes a cylindrical first wall having a hole into which a conduit is inserted, a second wall which encloses the first wall and opposes an oral cavity, and a gas flow path to a sample port which is configured by a gap between the first wall and the second wall (FIGS. 1 and 2 in PTL 1). The bite block is configured such that the respiration information collection adapter is attachable therein and detachable therefrom, and a prong is attached in the respiration information collection adapter (FIG. 4 in PTL 1). Further, oxygen is supplied to the prong from an oxygen supplying source (paragraph [0024] in PTL 1).

That is, the bite block described in PTL 1 is configured to be capable of performing both an oxygen administration and measurement of exhalation gas concentration of the subject. Additionally, a configuration (a mask and the like) in which therapeutic gas supply and exhalation gas measurement are simultaneously performed is used widely.

CITATION LIST

Patent Literature

[PTL 1]
Japanese Patent No. 5385599

Non Patent Literature

[NPL 1]
"CO2 sensor kit", Accessed: May 31, 2016], Internet URL:"http://www.nihonkohden.co.jp/iryo/products/monitor/01_bedside/tg970p.html"

SUMMARY OF INVENTION

Technical Problem

However, in the case of the configuration in which the insufflation of the therapeutic gas (preferably, oxygen gas) and the exhalation gas concentration measurement are simultaneously performed, there is a matter that the exhalation gas of the subject is diluted by the insufflated therapeutic gas and the exhalation gas concentration is hardly measured accurately.

The present invention has been made in consideration of the above situation, and an object thereof is to provide a gas sensor kit, in which exhalation gas concentration can be measured while reducing an effect of insufflated therapeutic gas, and a device wearable on a face.

Solution to Problem

According to an aspect of the invention, a gas sensor kit includes a gas sensor that measures a gas concentration of an exhalation gas of a subject, a gas introduction part that introduces the exhalation gas of the subject to the gas sensor and a gas supply unit that supplies a therapeutic gas to the subject. In the gas sensor kit, the gas supply unit includes a flow rate adjusting part that adjusts flow rate of the therapeutic gas.

The above-described gas sensor kit is configured to perform both a measurement of the exhalation gas concentration by the gas sensor and insufflation of the therapeutic gas. Preferably, the exhalation gas concentration is the carbon dioxide concentration of the exhalation gas. The gas supply unit has the flow rate adjusting part which performs adjustment such that the flow rate of the flowed-in therapeutic gas becomes low. By controlling the flow rate of the therapeutic gas to be low, the therapeutic gas is prevented from being vigorously blown to the nostril of the subject. Accordingly, also in the configuration in which the insufflation of the therapeutic gas is performed while measuring the exhalation gas concentration, it is possible to reduce an effect which the therapeutic gas has on the exhalation.

Advantageous Effects of Invention

The present invention can provide a gas sensor kit, in which exhalation gas concentration can be measured while reducing an effect of insufflated therapeutic gas, and a device wearable on a face.

BRIEF DESCRIPTION OF DRAWINGS

FIG. 1 is an exploded perspective view schematically illustrating a gas sensor kit 1 according to a first embodiment.

FIG. 2 is a conceptual view illustrating a state where the gas sensor kit 1 according to the first embodiment is attached.

FIG. 3 is a back view of a gas supply unit 40 according to the first embodiment.

FIG. 4 is a back view of the gas supply unit 40 according to the first embodiment.

FIG. 5 is a sectional view of the gas supply unit 40 according to the first embodiment.

FIG. 6 is a back view of the gas supply unit 40 according to the first embodiment.

FIG. 7 is a sectional view of the gas supply unit 40 according to the first embodiment.

FIG. 8 is a back view of the gas supply unit 40 according to the first embodiment.

FIG. 9A illustrate a cannula 50 according to the first embodiment.

FIG. 9B illustrate a cannula 50 according to the first embodiment.

DESCRIPTION OF EMBODIMENTS

First Embodiment

Hereinafter, the embodiment of the present invention will be described with reference to drawings. In the drawings, the same components are denoted by the same reference numerals and the same names, and the redundant explanation is not repeated. In addition, in order to facilitate understanding of the present invention, the size or the shape of each of components will be described after a proper adjustment.

FIG. 1 is an exploded perspective view schematically illustrating a gas sensor kit 1 according to this embodiment. The gas sensor kit 1 insufflates a therapeutic gas to a subject, and is a medical unit which measures an exhalation gas concentration. The gas sensor kit 1 includes a bite block 10, a nasal adapter 20, a gas sensor 30, and a gas supply unit 40. The therapeutic gas may be an oxygen gas or a hydrogen gas, and in the following description, an oxygen gas is adopted.

Incidentally, in the following description and drawings, the directions when the gas sensor kit 1 is attached on the subject are determined as follows. A right and left direction of a face of the subject when a state where the gas sensor kit 1 is attached on the subject is viewed from a front side is set as an X direction (a left-face direction is a positive X direction, and a right-face direction is a negative X direction). An upper and lower direction of the face of the subject is set as a Y direction (a vertex direction is a positive Y direction, and a chin direction is a negative Y direction). An intraoral direction of the subject is set as a negative Z direction, and a direction away from an oral cavity of the subject is set as a positive Z direction.

The bite block 10 is a tool which is inserted into the oral cavity when an inspection is performed by using an endoscope or a hard mirror. Incidentally, the bite block 10 is an example of the tool which is disposed in the vicinity of the oral cavity of the subject and is used together with the gas supply unit 40. For this reason, the gas sensor kit 1 may include a mask or the like instead of the bite block 10. The bite block 10 has a cylindrical shape, and has a connection mechanism which is connected with the nasal adapter 20.

The nasal adapter 20 is connected with the bite block 10, and is an adapter which is disposed in the vicinity of nostrils of the subject. Nasal tubes 21 and 22 are inserted into both nostrils of the subject. In addition, the nasal adapter 20 is connected with the gas sensor 30, and the exhalation gas of the subject is introduced to the gas sensor 30. That is, the nasal adapter 20 is one aspect of a gas introduction part which introduces the exhalation gas of the subject to the gas sensor 30.

The gas sensor 30 is configured to be attachable to and detachable from the nasal adapter 20. For example, the gas sensor 30 is connected with the nasal adapter 20 by fitting a concave portion having a light receiving window to the nasal adapter 20. The gas sensor 30 measures exhalation gas concentration of the subject. The exhalation gas concentration is the concentration of carbon dioxide in the following description, but may be other gas concentration. The gas sensor 30 has a light-emitting part and a light-receiving part, and calculates the concentration of the carbon dioxide based on the transmitted light of the exhalation gas of the subject. Since the carbon dioxide has a property to absorb strongly an infrared ray of a certain specific wavelength, the infrared light is strongly absorbed as the concentration of the carbon dioxide in the exhalation gas is higher, and the amount of the transmitted light is decreased. The gas sensor 30 may have any shape or structure as long as the concentration of the carbon dioxide of the exhalation gas is detected by using the property. The sensor kit disclosed in NPL 1 is an example as implementation.

The gas sensor 30 is configured to be attachable to and detachable from the gas supply unit 40. For example, a tube which extends from the gas sensor 30 or a casing of the gas sensor 30, and a casing of the gas supply unit 40 may be configured to be connected by being fitted to each other. Alternatively, a cutting hole or a claw may be provided in the gas supply unit 40 and be fitted to a boss and the like provided in the gas sensor 30, such that the gas supply unit 40 is connected with the gas sensor 30. In addition, the gas supply unit 40 may have such a structure that is connected with the nasal adapter 20. Also in this case, both may be connected by using the boss or the cutting hole. That is, the gas supply unit 40 may be configured to be attachable to and detachable from the gas sensor 30 or the nasal adapter 20.

The gas supply unit 40 supplies the therapeutic gas to the nostril of the subject. The gas supply unit 40 is connected with the nasal adapter 20 through the gas sensor 30, and is disposed in the vicinity of the nostril of the subject. The oxygen gas is supplied from an oxygen supplying source to the tube 41. The gas supply unit 40 has a cap-shaped main body 43 to cover the casing of the gas sensor 30. When the casing of the gas sensor 40 is made in the cap shape, the insufflated oxygen gas stays in the vicinity of the nostril of the subject, and thus the oxygen administration can be performed efficiently. The main body 43 is a vacant room in which the oxygen gas flows. The oxygen gas supplied from the tube 41 passes through a porous member 42, and then flows in the cap-shaped main body 43.

Subsequently, the description will be given about the state where the gas sensor kit 1 is attached. FIG. 2 is a view illustrating the state where the gas sensor kit 1 according to this embodiment is attached. That is, an enlarged view of a lower portion of the face of the subject on is shown in which the gas sensor kit 1 is being attached.

The bite block 10 is inserted into the oral cavity of the subject. The nasal tubes 21 (not illustrated in FIG. 2) and 22 of the nasal adapter 20 connected to the bite block 10 are inserted into both nostrils of the subject. The nasal tubes 21 and 22 may be disposed in a vicinity of the nostrils.

The gas supply unit 40 covers the main body of the nasal adapter 20 and the gas sensor 30, and is disposed between the nostril and a lip of the subject. For this reason, the gas supply unit 40 supplies the oxygen gas supplied from the tube 41 to the vicinity of the nostril of the subject. Herein, the gas supply unit 40 adjusts flow rate of the oxygen gas such that the supplied oxygen gas does not affect the detection of the exhalation gas concentration by the gas sensor 30. Hereinafter, the description will be given about such an adjusting mechanism.

FIG. 3 is a back view of the gas supply unit 40 which is a view when the gas supply unit 40 is seen from the negative Z direction. The above-described tube 41 introduces the oxygen gas. The oxygen gas flowed in from the tube 41 flows in a gas inflow port 44 which is a gas flow path between the main body 43 and the tube 41. The gas inflow port 44 is provided with the porous member 42 as one aspect of a flow rate adjusting part which adjusts the flow rate of the oxygen gas. In other words, the flow rate adjusting part lowers the flow rate. It is preferable that the flow rate adjusting part performs adjustment to lower the flow rate and to diffuse an inflow direction of the gas. For example, the porous member 42 is a sponge, and buffers the oxygen gas flowed in from the tube 41 to supply the oxygen gas with the low flow rate to the cap-shaped main body 43.

The porous member 42 performs adjustment to diffuse the inflow direction of the flowed-in oxygen gas. The porous member 42 is configured to have numerous openings, and generally, an opening direction thereof is not constant. For example, in a case where the porous member 42 is a sponge, the opening direction of the numerous openings configuring the sponge is not constant. For this reason, the inflow direction of the oxygen gas supplied from the porous member 42 becomes in a diffused state as illustrated by a dotted line arrow of FIG. 3.

As illustrated in FIG. 2, the main body 43 is disposed between the nostril and the lip of the subject. The oxygen gas in a state where the flow rate is sufficiently lowered by the porous member 42 flows in the main body 43. In addition, the oxygen gas flows in the main body 43 in a state where the inflow direction is diffused.

Next, the description will be given about the effect of the gas sensor kit 1 according to this embodiment. The gas sensor kit 1 is configured to perform both the measurement of the exhalation gas concentration through the gas sensor 30 and the insufflation of the oxygen gas. Here, the exhalation gas concentration is preferably the carbon dioxide concentration of the exhalation gas, and the oxygen gas is one aspect of the therapeutic gas. The gas supply unit 40 has the porous member 42 which performs adjustment such that the flow rate of the oxygen gas flowed in from the tube 41 is lowered. The porous member 42 is one aspect of the flow rate adjusting part. When the flow rate of the oxygen gas is controlled to be low, the oxygen gas is prevented from being vigorously blown to the nostril of the subject. Accordingly, even in the configuration in which the insufflation of the oxygen gas is performed while measuring the exhalation gas concentration, it is possible to reduce an effect which the oxygen gas has on the exhalation.

The porous member 42 is configured to have numerous micropores, so as to have permeability and act as a damping member with respect to the flowed-in oxygen gas. For this reason, the oxygen gas can be taken in the vicinity of the nostril of the subject, and the effect which the oxygen gas has on the exhalation can be reduced. In addition, the porous member 42 is made of a general material such as a sponge, and thus the above-described effect can be achieved without increasing costs. Further, in the case of using a sponge, the sponge is a light material so that the wearing load on the subject is small.

The opening direction of the micropores configuring the porous member 42 is not constant, and thus as illustrated in FIG. 3, the inflow direction of the oxygen gas is diffused. Accordingly, the oxygen gas is prevented from converging into one point, so that the effect which the oxygen gas has on the exhalation can be reduced.

The porous member 42 is one aspect of the flow rate adjusting part which adjusts the flow rate of the oxygen gas, and may be another aspect. Hereinafter, a description of a modification will be given.

(Modification 1)

In a first modification, the flow rate adjusting part is configured by a columnar body 45 and a slit 46. Hereinafter, the configuration will be described with reference to FIGS. 4 and 5. FIG. 4 is a back view of the gas supply unit 40 according to the modification (a view when the gas supply unit 40 is seen from the negative Z direction). FIG. 5 is a sectional view taken along line A-A of the gas supply unit 40 in FIG. 4.

The main body 43 is provided with the columnar body 45 having the slit 46. That is, the columnar body 45 and the slit 46 are provided in a position of opposing the tube 41. As illustrated in FIG. 5, the columnar body 45 has a shape with a height (a length in a Z axial direction). In this example, the two slits 46 are provided in the columnar body 45, but the number of the slits 46 may be arbitrary.

The oxygen gas flowed in from the tube 41 flows in through the slit 46. The columnar body 45 acts as a wall with respect to the oxygen gas flowed in from the tube 41. For this reason, the oxygen gas blown to the columnar body 45 is forced back to stay in the main body 43. The staying oxygen gas moves to oppose the oxygen gas newly flowed in from the tube 41, and thus the flow rate of the oxygen gas is lowered.

In this example shown in FIGS. 4 and 5, the columnar body 45 and the slit 46 are provided in a substantially central portion of the main body 43 in the X direction, which is the vicinity of the center in the X axial direction. However, the invention is not necessarily limited thereto, and may be provided closer to the tube 41 than the substantially central portion.

Also in this modification, the columnar body 45 and the slit 46 adjust the flow rate of the oxygen gas flowed in from the tube 41 to be lowered. Accordingly, in a state where the effect of the oxygen gas flowed in from the tube 41 is cancelled, it is possible to detect the exhalation gas concentration of the subject.

(Modification 2)

In a second modification, the flow rate adjusting part is configured by a plurality of columnar bodies 47. Hereinafter, the configuration will be described with reference to FIGS. 6 and 7. FIG. 6 is a back view of the gas supply unit 40 according to the modification, which is a view when the gas supply unit 40 is seen from the negative Z direction. FIG. 7 is a sectional view taken along line A-A of the gas supply unit 40 in FIG. 6.

The main body 43 which is a vacant room having a cap shape in which the oxygen gas flows is provided in the plurality of columnar bodies 47. Incidentally, in an example of FIG. 6, eight columnar bodies 47 are provided, but the number of the columnar bodies 47 may be arbitrary. That is, at least one columnar body 47 may be provided in the main body 43. In addition, the shape of the columnar body 47 may be a columnar shape, or may be an angular columnar shape. In addition, the size of the columnar body 47 may be arbitrary.

The respective columnar bodies 47 act as walls with respect to the oxygen gas flowed in from the tube 41. That is, the oxygen gas blown to the columnar body 47 stays in the main body 43 and the inflow direction thereof is changed. Accordingly, the inflow direction of the oxygen gas flowed in from the tube 41 is diffused, and the flow rate is lowered.

As illustrated in FIG. 8, the flow rate adjusting part may be a streamlined flow path 48 which has meander shape and guides the introduced oxygen gas. In FIG. 8, an example in which the flow path 48 meanders is illustrated, but the invention is not necessarily limited thereto. The flow rate adjusting part may be adopted as long as the oxygen gas is introduced in a direction different from the inflow direction of the oxygen gas flowed in from the tube 41. Accordingly, the flowed-in oxygen gas advances with meandering, and thus the flow rate is controlled to be lowered.

Hereinbefore, the invention made by this inventor is described in specific based on the embodiment. However, the present invention is not limited to the above-described embodiment, and the invention may be modified variously without departing from the spirit and scope of the invention.

In the above description, the gas sensor kit 1 has a configuration in which the bite block which the subject bites is connected with the gas sensor and the like, but the invention is not limited thereto. That is, as far as the gas sensor kit 1 is configured to perform the gas insufflation and the measurement of the exhalation gas concentration, and the gas sensor may be connected with the oxygen mask or the oxygen cannula other than the bite block of FIG. 1.

In theory, the flow rate adjusting part such as the porous member 42 can be formed in the tube 41. That is, the gas sensor kit 1 may be configured to have the flow rate adjusting part which adjusts the flow rate of the therapeutic gas in the gas flow path from a supply source of the therapeutic gas to the vicinity of the nostril of the subject.

In the above-described description about FIG. 1 and the like, the gas measurement is performed in a mainstream type. However, the invention is not necessarily limited thereto, and the above-described technology may be applied to a sidestream type gas measurement. That is, the exhalation gas of the subject may be introduced to an external gas measuring unit (above-described gas sensor 30) through the tube (one aspect of the gas introduction part) and the like, and the above-described gas supply unit 40 may be used. Also in the configuration, it is possible to measure the exhalation gas concentration in which the effect of the insufflated oxygen gas is reduced.

FIGS. 9A and 9B are views illustrating the cannula 50 as another example of the gas introduction part. FIG. 9A is a perspective view of the cannula 50, and FIG. 9B is a top view of the cannula 50 when seen from the positive Y direction. As illustrated, the two nasal tubes 51 and 52 which are inserted into the nostril are provided. In addition, an oxygen supply port 53 is provided which is disposed between the nasal tubes 51 and 52, and supplies oxygen in the positive Y direction. The cannula 50 is used instead of the above-described nasal adapter 20, and the gas supply unit 40 is attached in the cannula 50 and supplies the oxygen gas to a patient. In addition, the gas sensor 30 may measure the exhalation gas concentration by using the exhalation gas inhaled from the nasal tubes 51 and 52 through the tubes 54 and 55.

It is construed that the gas sensor kit 1 includes device wearable on the face (bite block 10, nasal adapter 20, and gas supply unit 40) which is attached on the face of the subject to manage the respiratory state or the state of the oral cavity, and the gas sensor 30 which measures the exhalation gas concentration. The configuration of device wearable on the face may be arbitrary. For example, there may be adopted a configuration in which the bite block 10 is not provided, or a configuration in which an oxygen sensor is provided instead of the bite block 10.

The present application is based on Japanese Patent Application No. 2016-117759, filed on Jun. 14, 2016, the entire contents of which are incorporated herein by reference.

INDUSTRIAL APPLICABILITY

There is provided with a gas sensor kit, in which exhalation gas concentration can be measured while reducing an effect of insufflated therapeutic gas, and a device wearable on a face.

REFERENCE SIGNS LIST

1: gas sensor kit
10: bite block
20: nasal adapter
21,22: nasal tube
30: gas sensor
40: gas supply unit
41: tube
42: porous member
43: main body
44: gas inflow port
45: columnar body
46: slit
47: columnar body
48: flow path
50: cannula

The invention claimed is:
1. A gas sensor kit comprising:
a gas sensor that measures a gas concentration of an exhalation gas of a subject;
a gas introduction part that introduces the exhalation gas of the subject to the gas sensor; and
a gas supply unit that supplies a therapeutic gas to the subject,
wherein the gas supply unit includes a flow rate adjusting part that is configured to impede a flow of the therapeutic gas to the subject to thereby lower a flow rate of the therapeutic gas to the subject, wherein the flow rate adjusting part is a porous member that is disposed in a gas inflow port from a supply source of the therapeutic gas.
2. The gas sensor kit according to claim 1, wherein the porous member includes a sponge.
3. The gas sensor kit according to claim 1, wherein the flow rate adjusting part adjusts an inflow direction of the therapeutic gas to be diffused.
4. A device wearable on a face comprising:
a gas introduction part that introduces an exhalation gas of a subject to a gas sensor that measures gas concentration of the exhalation gas of the subject; and
a gas supply unit that is configured to be attachable to and detachable from the gas sensor or the gas introduction part, and supplies therapeutic gas to the subject,
wherein the gas supply unit includes a flow rate adjusting part that is configured to impede a flow of the therapeutic gas to the subject to thereby lower a flow rate of the therapeutic gas to the subject, wherein the flow rate adjusting part is a porous member that is disposed in a gas inflow port from a supply source of the therapeutic gas.
5. A gas sensor kit that measures exhalation gas concentration of a subject while insufflating therapeutic gas to the subject, the gas sensor kit comprising:
a flow rate adjusting part that is configured to impede a flow of the therapeutic gas to the subject to thereby lower a flow rate of the therapeutic gas flowing in a gas flow path from a supply source of the therapeutic gas to the subject,
wherein the flow rate adjusting part is a porous member that is disposed in a gas inflow port from a supply source of the therapeutic gas.
6. The gas sensor kit according to claim 1, wherein the gas supply unit comprises a cannula.
7. The gas sensor kit according to claim 1, wherein the gas supply unit comprises a cap-shaped body that covers a casing of the gas sensor and supplies the therapeutic gas to the subject.
8. The gas sensor kit according to claim 7, wherein the cap-shaped body defines a room, and the flow rate adjusting part is located within the room.
9. The gas sensor kit according to claim 1, wherein the gas introduction part comprises a tube that introduces the exhalation gas of the subject to the gas sensor.
10. A gas sensor kit comprising:
a gas sensor;

a gas introduction tube that introduces an exhalation gas of a subject to the gas sensor; and a gas supply tube that supplies a therapeutic gas to the subject; and a flow rate adjusting part that is configured to impede a flow of the therapeutic gas to the subject to thereby lower a flow rate of the therapeutic gas supplied to the subject, wherein the flow rate adjusting part is a porous member that is disposed in a gas inflow port from a supply source of the therapeutic gas.

11. A gas sensor kit comprising:

a gas sensor that measures a gas concentration of an exhalation gas of a subject;

a gas introduction part that introduces the exhalation gas of the subject to the gas sensor; and a gas supply unit that supplies a therapeutic gas to the subject, wherein the gas supply unit includes a flow rate adjusting part that is configured to impede a flow of the therapeutic gas to the subject to thereby lower a flow rate of the therapeutic gas to the subject, and a cap-shaped body that covers a casing of the gas sensor and supplies the therapeutic gas to the subject, and wherein the cap-shaped body defines a room, and the flow rate adjusting part is located within the room.

12. A device wearable on a face comprising:

a gas introduction part that introduces an exhalation gas of a subject to a gas sensor that measures gas concentration of the exhalation gas of the subject; and a gas supply unit that is configured to be attachable to and detachable from the gas sensor or the gas introduction part, and supplies therapeutic gas to the subject, wherein the gas supply unit includes a flow rate adjusting part that is configured to impede a flow of the therapeutic gas to the subject to thereby lower a flow rate of the therapeutic gas to the subject, and a cap-shaped body that covers a casing of the gas sensor and supplies the therapeutic gas to the subject, and wherein the cap-shaped body defines a room, and the flow rate adjusting part is located within the room.

13. A gas sensor kit that measures exhalation gas concentration of a subject while insufflating therapeutic gas to the subject, the gas sensor kit comprising:

a flow rate adjusting part that is configured to impede a flow of the therapeutic gas to the subject to thereby lower a flow rate of the therapeutic gas flowing in a gas flow path from a supply source of the therapeutic gas to the subject, and a cap-shaped body that supplies the therapeutic gas to the subject, wherein the cap-shaped body defines a room, and the flow rate adjusting part is located within the room.

14. A gas sensor kit comprising:

a gas sensor;

a gas introduction tube that introduces an exhalation gas of a subject to the gas sensor;

a cap-shaped body that covers a casing of the gas sensor and supplies a therapeutic gas to the subject; and a flow rate adjusting part that is configured to impede a flow of the therapeutic gas to the subject to thereby lower a flow rate of the therapeutic gas supplied to the subject, wherein the cap-shaped body defines a room, and the flow rate adjusting part is located within the room.

* * * * *